(12) United States Patent
Van Iderstine

(10) Patent No.: US 7,942,155 B2
(45) Date of Patent: May 17, 2011

(54) PORTABLE ORAL HYGIENE SYSTEM

(76) Inventor: Richard Van Iderstine, Detroit, MI (US)

( * ) Notice: Subject to any disclaimer, the term of this patent is extended or adjusted under 35 U.S.C. 154(b) by 58 days.

(21) Appl. No.: 12/411,084

(22) Filed: Mar. 25, 2009

(65) Prior Publication Data

US 2009/0178691 A1    Jul. 16, 2009

Related U.S. Application Data

(63) Continuation of application No. 11/394,226, filed on Mar. 31, 2006, now abandoned.

(60) Provisional application No. 60/666,613, filed on Mar. 31, 2005.

(51) Int. Cl.
*A45D 44/18* (2006.01)

(52) U.S. Cl. ........................................ 132/309; 132/321

(58) Field of Classification Search ................... 132/309, 132/311, 294, 297, 321, 322, 324; 206/235, 206/394, 409, 503, 227, 581, 570, 574; 222/129, 222/192
See application file for complete search history.

(56) References Cited

U.S. PATENT DOCUMENTS

| 2,601,244 | A | 6/1952 | Boulicault |
| 4,919,156 | A | 4/1990 | Gipson |
| 5,044,386 | A | 9/1991 | Nelson |
| 5,865,195 | A | 2/1999 | Carter |
| 6,016,916 | A | 1/2000 | Ortner |
| 6,253,773 | B1 | 7/2001 | Ingemann |
| 6,526,991 | B2 | 3/2003 | Bodwalk |

*Primary Examiner* — Rachel R Steitz
(74) *Attorney, Agent, or Firm* — Duane Morris, LLP

(57) ABSTRACT

A novel oral hygiene system comprised of a plurality of substantially cylindrical pieces removably attached to each other that may be adapted to contain breath spray, dental floss, a dental floss cutter, toothpicks and breath mints in a compact and highly portable container.

11 Claims, 5 Drawing Sheets

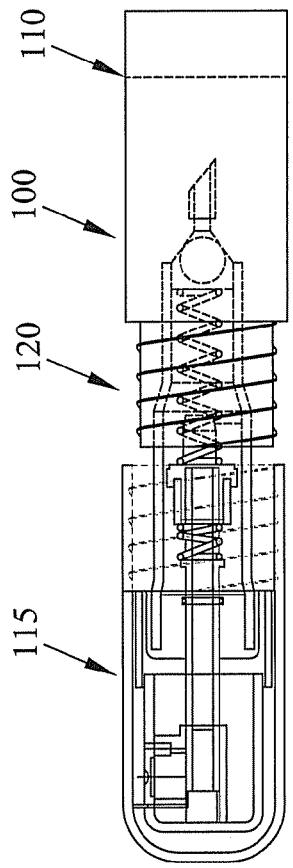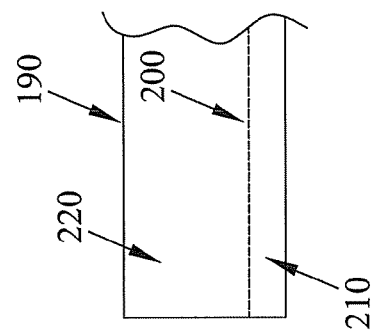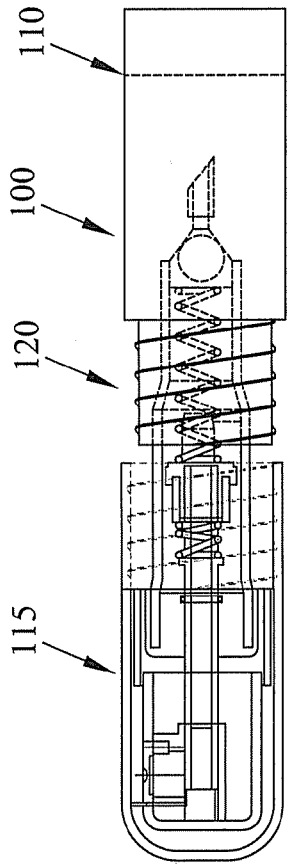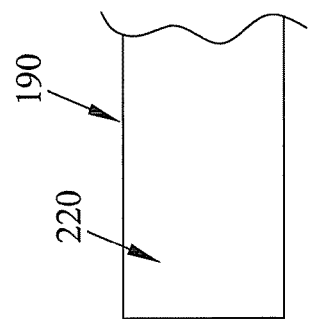
Figure 2
Figure 3

PORTABLE ORAL HYGIENE SYSTEM

CROSS-REFERENCE TO RELATED APPLICATIONS

The instant application is a continuation of and claims the priority benefit of co-pending application Ser. No. 11/394,226, filed Mar. 31, 2006 now abandoned which claims the filing-date priority of the provisional Application No. 60/666,613 filed Mar. 31, 2005, the entirety of each are incorporated herein in their entirety.

BACKGROUND

Proper oral hygiene is important to maintain healthy teeth and gums. Although many individuals practice good oral hygiene when home, they often do not have the necessary dental equipment and supplies available to them when traveling or away from home for brief periods. It would be a benefit to these individuals to have an oral hygiene system that included the dental equipment and supplies to continue to practice proper oral hygiene when away from home. Additionally, it can often be desirable to perform oral hygiene procedures such as flossing and using a breath spray or mouthwash solution after dining at a public restaurant or in preparation for a business meeting. It would therefore be an additional benefit to have an oral hygiene system that could easily be carried and concealed in a pocket or purse.

SUMMARY

The present disclosure is directed to an apparatus that satisfies this need. In one embodiment, the apparatus comprises a first cylindrical piece adapted to attach a push-down spray valve assembly and contain a liquid breath spray. A second cylindrical piece may be removably attached to the first piece by means of, for example, a bayonet mount, screw threads, or a press fit. The second piece may be adapted to contain a spool of dental floss and a floss cutter. A third cylindrical piece may be removably attached to the second piece by means of, for example, a bayonet mount, screw threads, or a press fit. The third piece may be subdivided into two compartments, one containing breath mints and the other containing toothpicks.

In another embodiment, the apparatus comprises a first cylindrical piece adapted to attach a push-down spray valve assembly and contain a liquid breath spray. A second cylindrical piece may be removably attached to the first piece by means of, for example, a bayonet mount, screw threads, or a press fit. The second piece may be adapted to contain toothpicks and a portion of a spool of dental floss. A third cylindrical piece may be removably attached to the second piece by means of, for example, a bayonet mount, screw threads, or a press fit. The third piece may be adapted to hold a floss cutter. A fourth cylindrical piece may be removably attached to the third piece by means of, for example, a bayonet mount, screw threads, or a press fit. The fourth piece may be adapted to contain breath mints.

One object of the present disclosure is to provide an oral hygiene system comprising a generally pen-shaped housing containing breath spray, dental floss, a floss cutter, toothpicks and breath mints.

Another object of the disclosure is to nest the breath spray, dental floss & floss cutter, toothpicks and breath mints in a single container in order to conserve space, such as a container generally shaped like a pen with a clip for attaching the container to, for example, a shirt pocket.

Yet another object of the present disclosure is to provide a portable, easily concealable apparatus that dispenses breath spray, dental floss, a floss cutter, toothpicks and breath mints wherever an individual desires.

Still other benefits and advantages of the disclosure will become apparent to those skilled in the art upon a reading and understanding of the following detailed specification.

BRIEF DESCRIPTION OF THE DRAWINGS

FIG. 2 is a schematic side view illustrating an exemplary embodiment of an oral hygiene system in accordance with the present disclosure.

FIG. 3 is a schematic side view rotated 90 degrees from the view in FIG. 2 illustrating an exemplary embodiment of an oral hygiene system in accordance with the present disclosure.

DETAILED DESCRIPTION

In this disclosure, numerous specific details are set forth to provide a sufficient understanding of the present invention. However, those skilled in the art will appreciate that the present invention may be practiced without such specific details or with obvious substitutions. In other instances, well-known elements have been illustrated in schematic or block diagram form in order not to obscure the present invention in unnecessary detail. Additionally, some details have been omitted inasmuch as such details are not considered necessary to obtain a complete understanding of the present invention, and are considered to be within the understanding of persons of ordinary skill in the relevant art. As one skilled in the art will appreciate, components may be referred to by different names. This document does not intend to distinguish between components that differ in name, but not function.

Figure 1:
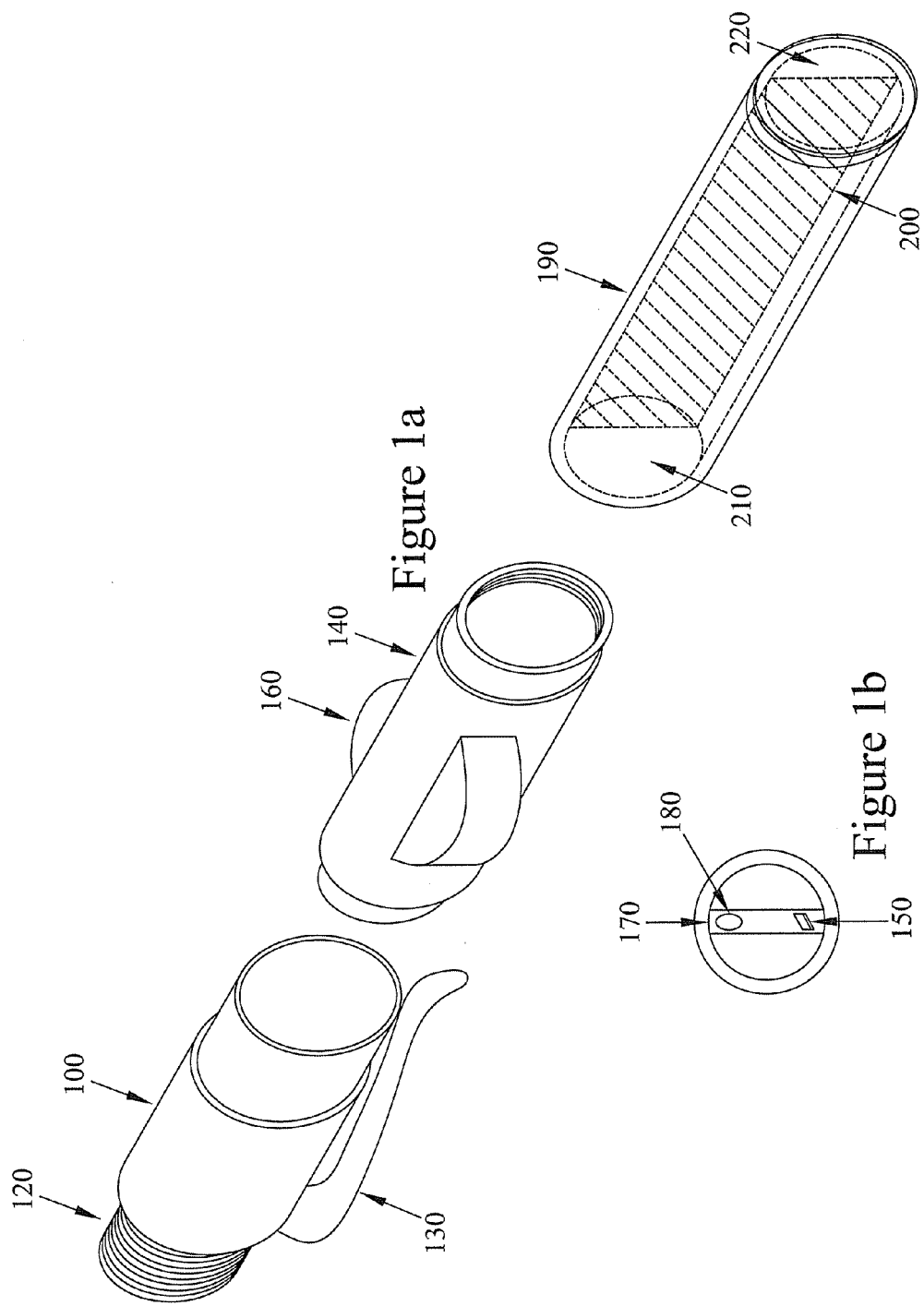
FIG. 1a is an exploded view illustrating an exemplary embodiment of an oral hygiene system in accordance with the present disclosure.
FIG. 1b is a top view illustrating a top portion of the middle piece of an oral hygiene system in FIG. 1a in accordance with the present disclosure.

FIG. 1a is an isometric view illustrating an exemplary embodiment of an oral hygiene system in accordance with the present disclosure. As shown in FIG. 1a, the system is composed of three substantially cylindrical pieces 100, 140 and 190 removably attached to each other. When fully assembled, the system may be approximately 4"-6" in length and approximately 0.4-0.6" in diameter. Alternatively, the system may be somewhat larger or smaller either in length or diameter. These pieces may be made of injection molded plastic, silicon or any other suitable material.

The first cylindrical piece 100 has a hollow internal cavity containing a transverse interior partition 110, as shown in FIGS. 2 and 3, that creates an upper cavity and a lower cavity. The upper portion also has a threaded upper portion 120. A standard push-down spray valve assembly 115 may be mated with the threaded portion of the first piece 100 to create a container. This container may be filled with any oral hygiene liquid such as breath spray, mouth wash, oral pain reliever such as Anbesol®, or sore throat reliever such as Chloraseptic®. When coupled with the push-down spray valve assembly, the first piece is a portable, refillable breath spray container that can conveniently be used by the owner anywhere. Additionally, a clasp 130, similar to those found on pens, may be attached to the first piece. This clasp 130 will allow the system to be conveniently attached to a garment for ease of transportation. In an alternative embodiment the clasp 130 could be attached to a cap on the push-down spray valve assembly, the second piece 140, or the third piece 190.

As shown in FIG. 1a, the second cylindrical piece 140 is adapted to hold a spool of dental floss (not shown) and a dental floss cutter 150. It should be understood that any type of dental floss, such as dental floss for braces, or other dental hygiene tool could be substituted for the spool of dental floss. The second piece 140 may be attached to the first piece by any removable means such as a bayonet mount, screw threads, or a press fit. The second piece 140 may have a disc-shaped protrusion 160 adapted to hold a disc-shaped spool of dental floss. In an alternative embodiment the second piece 140 may lack the drum-shaped extrusion and may instead be adapted to hold a cylindrical spool of dental floss. As illustrated in FIG. 1b, the second piece 140 may have a crosspiece or cap 170 attached across the upper rim. The crosspiece 170 may contain a suitable mounting structure for attaching the dental floss cutter 150. This crosspiece may also have an aperture 180 for feeding the dental floss through on one side, and the dental floss cutter 150 may be mounted to the opposite side for capturing and cutting the dental floss. In an alternative embodiment there may be a detent (not shown) between the aperture 180 and the dental floss cutter 150 to make it easier to grasp the dental floss. The dental floss cutter 150 may be composed of metal or plastic or any other appropriate material.

Figure 4:
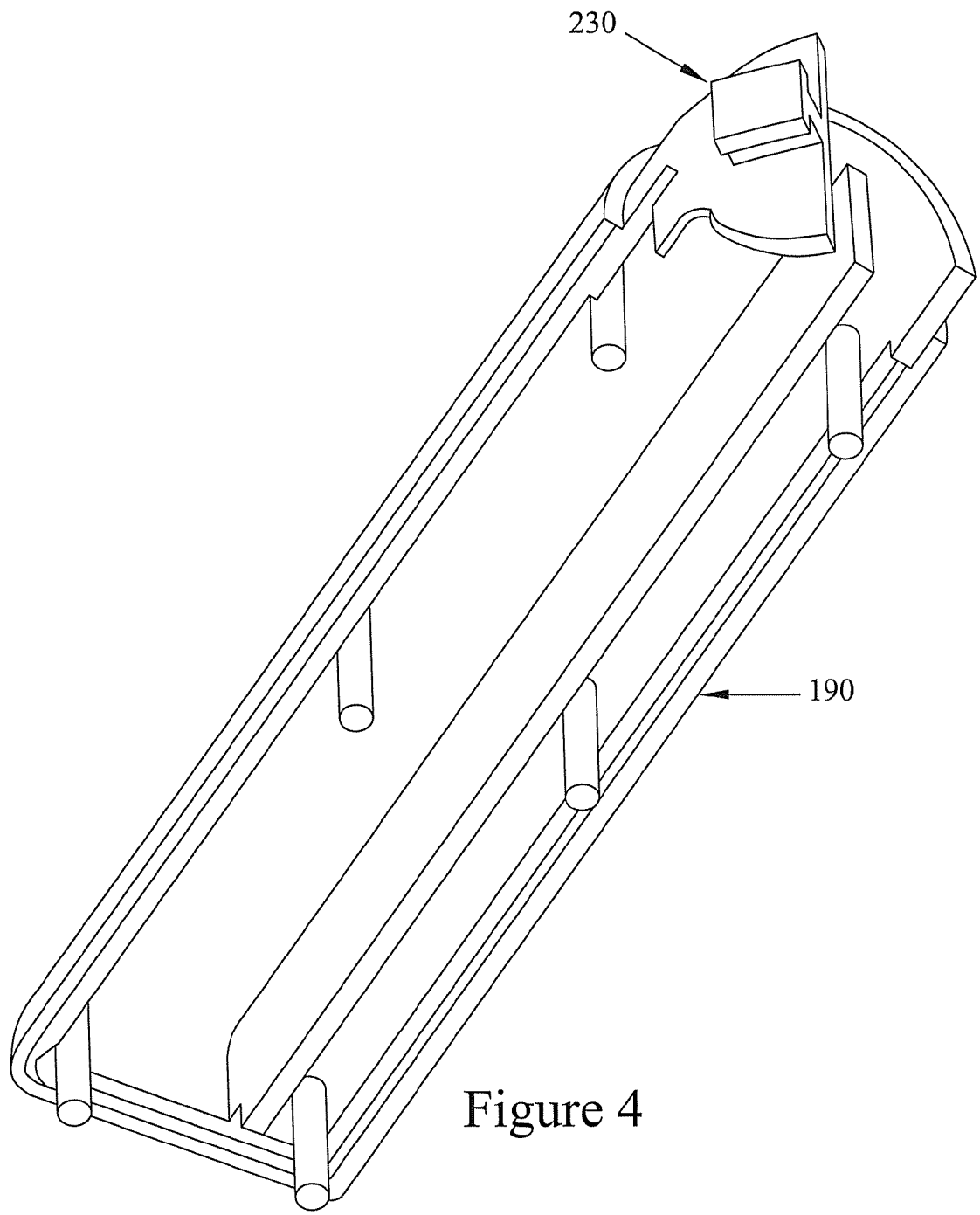
FIG. 4 is a pictorial view illustrating a component of an exemplary embodiment of an oral hygiene system in accordance with the present disclosure.
Figure 5:
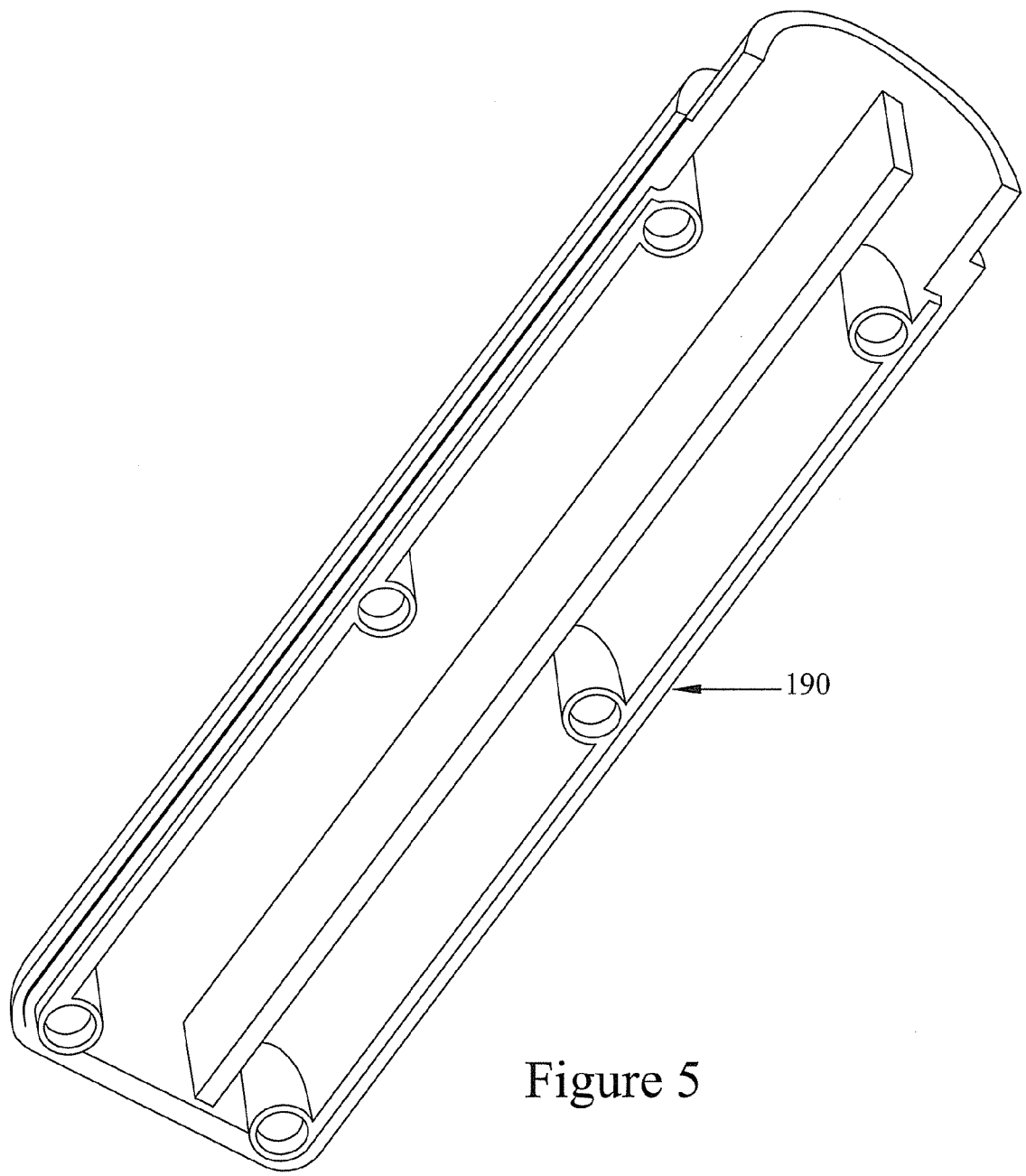
FIG. 5 is a pictorial view illustrating another component of an exemplary embodiment of an oral hygiene system in accordance with the present disclosure.

The third cylindrical piece 190 shown in FIG. 1a may be attached to the second piece 140 by any removable means such as a bayonet mount, screw threads, or a press fit. The third piece 190 has a hollow internal cavity containing a longitudinal interior partition 200, as shown in FIG. 1a and 2 that creates two cavities 210 and 220. The cavities may be dissimilar in size, with the cavity 210 adapted to hold breath mints being larger than the cavity 220 adapted to hold toothpicks. FIGS. 4 and 5 illustrate an exemplary embodiment of how the two halves of the third piece 190 may be constructed. Additionally, as shown in FIG. 4, the cavity 210 adapted to hold breath mints may have a hinged cover 230 to contain the mints. In an alternative embodiment, the cavities 210 and 220 may be the same size, or the cavity 210 adapted to hold breath mints may be smaller than the cavity 220 adapted to hold the toothpicks. In another alternative embodiment the third piece 190 could be adapted to incorporate a small LED flashlight, an ink pen, or any other small instrument.

Figure 6:
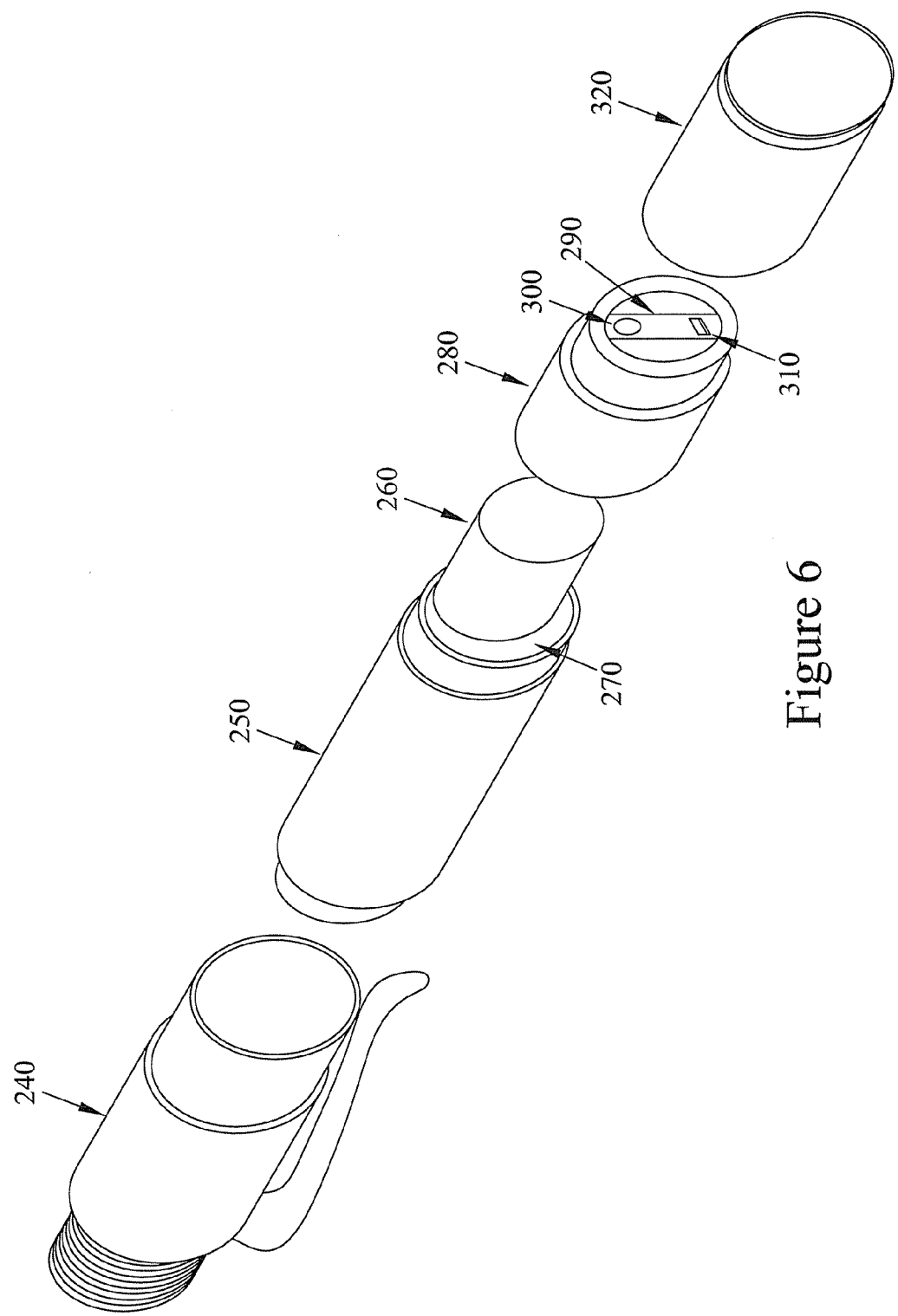
FIG. 6 is an exploded view illustrating another exemplary embodiment of an oral hygiene system in accordance with the present disclosure.

FIG. 6 is an exploded view illustrating a different exemplary embodiment of an oral hygiene system in accordance with the present disclosure. As shown in FIG. 6, the system is composed of four substantially cylindrical pieces 240, 250, 280, and 320 removably attached to each other. The first cylindrical piece 240 may be identical to the first piece 100 shown in FIG. 1a.

As shown in FIG. 6, the second cylindrical piece 250 is adapted to hold a spool of dental floss and toothpicks. The second piece 250 may be attached to the first piece by any removable means such as a bayonet mount, screw threads, or a press fit. The second piece 250 may be adapted to hold part of a cylindrical spool of dental floss within a cylindrical insert 260. In an alternative embodiment (not shown), the second piece 250 may have a disc-shaped protrusion adapted to hold a disc-shaped spool of dental floss. The cylindrical insert 260 adapted to contain a spool of dental floss may be mounted off-center within the second piece 250, thereby creating a crescent shaped channel 270 along one edge of the cylindrical insert 260. Toothpicks may easily be stored in this crescent shaped channel 270.

As shown in FIG. 6, the third piece 280 may be attached to the second piece by any removable means such as a bayonet mount, screw threads, or a press fit and may be adapted to hold part of the cylindrical spool of dental floss and a dental floss cutter 310. The third piece 280 may have a crosspiece or cap 290 attached across the upper rim. The cap 290 may contain a suitable mounting structure for attaching the dental floss cutter 310. The cap may have an aperture 300 for feeding the dental floss through on one side, and the dental floss cutter 310 attached to the opposite side for capturing and cutting the dental floss. In an alternative embodiment there may be a detent (not shown) between the aperture 300 and the dental floss cutter 310 to make it easier to grasp the dental floss. The dental floss cutter may be composed of metal or plastic or any combination thereof.

The fourth piece 320 shown in FIG. 6 may be a cylinder with a bottom cap or a solid bottom. Thus the fourth piece may be adapted to hold breath mints. The fourth piece 320 may be attached to the third piece 310 by any removable means such as a bayonet mount, screw threads, or a press fit. The fourth piece may have a hinged cover (not shown) to contain the mints. In an alternative embodiment the fourth piece 320 could be adapted to incorporate a small LED flashlight, an ink pen, or any other small instrument.

It is clear from the above that the objects of the invention have been fulfilled. While the components of an oral hygiene system are shown as having consistent dimensions in the various figures, the proportions shown are exaggerated for clarity. They are illustrative only and may be altered without notice. For instance, the first piece 100 can be proportionally shorter than shown and second piece 140 and third piece 190 can be longer. Additionally, while the disclosure and the figures describe substantially cylindrical pieces, one of skill in the art would readily understand that the pieces could have other cross-sectional shapes such as, for example, triangular, square, hexagonal or octagonal. The disclosure is intended solely to teach the concepts of the invention to one skilled in the art and is not limiting of the scope of the invention which is the province of the appended claims.

It is noted that the embodiments of an oral hygiene system described herein in detail for exemplary purposes may be subject to many different variations in structure, design, application and methodology. Because many varying and different embodiments may be made within the scope of the inventive concepts herein taught, and because many modifications may be made in the embodiment herein detailed in accordance with the descriptive requirements of the law, it is to be interpreted as illustrative and not in a limiting sense.

I claim:
1. An oral hygiene system comprising:
    a first substantially cylindrical piece defining a first volume, said first piece comprising:
    a threaded upper portion; and
    a transverse interior partition,
        wherein said threaded upper portion is mated with an assembly having a first end which is threadably engaged with said threaded upper portion and a second end comprising a push-down spray valve, wherein said first volume comprises breath spray and wherein said breath spray is withdrawn from said first volume by said push-down spray valve;

a second substantially cylindrical piece defining a second volume adapted to receive a spool of dental floss wherein said second piece is removably attached to said first piece; and a third substantially cylindrical piece defining a third volume adapted to receive a plurality of toothpicks and a plurality of breath mints wherein said third piece is removably attached to said second piece.

2. The system of claim 1 wherein said second piece comprises a crosspiece attached across an upper rim of said second piece, said crosspiece having:

a hole therethrough for passing dental floss from one side of the crosspiece to the opposite side of the crosspiece; and a mount for receiving a dental floss cutter.

3. The system of claim 2 further comprising a dental floss cutter attached to said mount.

4. The system of claim 1 wherein said third piece comprises a substantially longitudinal partition attached to said third piece and dividing said third volume into two compartments.

5. The system of claim 1 further comprising a clasp attached to said oral hygiene system for slideably attaching said oral hygiene system to a garment.

6. The system of claim 1 wherein said second piece is removably attached to said first piece by an attachment apparatus selected from the group consisting of: bayonet mount, screw threads, and press fit.

7. The system of claim 1 wherein said third piece is removably attached to said second piece by an attachment apparatus selected from the group consisting of: bayonet mount, screw threads, and press fit.

8. The system of claim 1 wherein said oral hygiene system is portable.

9. The system of claim 1 wherein said first piece is removable and separately usable as a portable container for breath spray.

10. An oral hygiene system comprising:

a first substantially cylindrical piece defining a first volume, said first piece having a transverse interior partition and a threaded upper portion which is mated with an assembly having a first end which is threadably engaged with said threaded upper portion and a second end comprising a push-down spray valve;

a second substantially cylindrical piece defining a second volume adapted to receive a spool of dental floss wherein said second piece is removably attached to said first piece, said second piece comprising a crosspiece attached across an upper rim of said second piece, said crosspiece having:

a hole therethrough for passing dental floss from one side of the crosspiece to the opposite side of the crosspiece; and a dental floss cutter attached to said crosspiece;

a third substantially cylindrical piece defining a third volume, said third piece comprising a substantially longitudinal partition attached to said third piece and dividing said third volume into a first compartment for receiving breath mints and a second compartment for receiving tooth picks; and a clasp attached to said oral hygiene system for slideably attaching said oral hygiene system to a garment, wherein said first volume comprises breath spray and wherein said breath spray is withdrawn from said first volume by said push-down spray valve, wherein said first piece is removable and separately usable as a portable, refillable container for breath spray, wherein said second piece is removably attached to said first piece by an attachment apparatus selected from the group consisting of: bayonet mount, screw threads, and press fit, and wherein said third piece is removably attached to said second piece by an attachment apparatus selected from the group consisting of: bayonet mount, screw threads, and press fit.

11. The system of claim 9 wherein said first piece is a refillable container for breath spray.

* * * * *